United States Patent
Hu et al.

(10) Patent No.: US 11,629,336 B2
(45) Date of Patent: Apr. 18, 2023

(54) METHOD OF PREPARING CROSSLINKED HYDROGELS, RESULTING MUSCLE STEM CELL CULTURE MEDIA, AND METHODS OF USE

(71) Applicant: Jiangnan University, Wuxi (CN)

(72) Inventors: Jing Hu, Wuxi (CN); Jian Yin, Wuxi (CN); Xiang Wang, Wuxi (CN)

(73) Assignee: JIANGNAN UNIVERSITY, Wuxi (CN)

(*) Notice: Subject to any disclaimer, the term of this patent is extended or adjusted under 35 U.S.C. 154(b) by 0 days.

(21) Appl. No.: 17/846,227

(22) Filed: Jun. 22, 2022

(65) Prior Publication Data

US 2022/0333080 A1    Oct. 20, 2022

Related U.S. Application Data

(63) Continuation of application No. PCT/CN2021/139539, filed on Dec. 20, 2021.

(30) Foreign Application Priority Data

Jan. 21, 2021 (CN) .......................... 202110080342.9

(51) Int. Cl.
*C12N 5/077* (2010.01)
*C08J 3/075* (2006.01)
(Continued)

(52) U.S. Cl.
CPC ............ *C12N 5/0658* (2013.01); *C08J 3/075* (2013.01); *C12N 9/1044* (2013.01); *A23L 13/00* (2016.08);
(Continued)

(58) Field of Classification Search
CPC .............. C12N 5/0658; C12N 2537/10; C12N 2533/74; C12N 2533/54; C12N 9/1044;
(Continued)

(56) References Cited

U.S. PATENT DOCUMENTS

2004/0063206 A1    4/2004   Rowley et al.

FOREIGN PATENT DOCUMENTS

| CN | 102688525 A | 9/2012 |
| CN | 103421199 A | 12/2013 |

(Continued)

OTHER PUBLICATIONS

Ravikumar, Heparan Sulfate Proteoglycans: Key Mediators of Stem Cell Function, Frontiers in Cell and Developmental Biology, vol. 8, Article 581213, doi: 10.3389/fcell.2020.581213. (Year: 2020).*

*Primary Examiner* — Kevin S Orwig
*Assistant Examiner* — John Michael Cronin
(74) *Attorney, Agent, or Firm* — IPRO, PLLC; Na Xu

(57) ABSTRACT

Described is a crosslinked hydrogel for muscle stem cell culture and a preparation method and use thereof. The preparation method includes: dissolving collagen to prepare a solution and adding alginate and heparan sulfate proteoglycan and uniformly mixing with the collagen solution; adding ε-PL and TGase into the solution, uniformly stirring, and putting a slurry into a mold for crosslinking to obtain the hydrogel. The hydrogel is prepared by linking the collagen, the polylysine, and the heparan sulfate proteoglycan using the TGase to form covalent crosslinking, and forming a compact three-dimensional "egg box" network structure through a physical electrostatic interaction between the polylysine and the alginate.

9 Claims, 5 Drawing Sheets

(51) Int. Cl.
*A23L 13/00* (2016.01)
*C12N 9/10* (2006.01)
*A23L 17/00* (2016.01)

(52) U.S. Cl.
CPC ........... *A23L 17/00* (2016.08); *C08J 2305/04* (2013.01); *C08J 2405/04* (2013.01); *C08J 2405/10* (2013.01); *C12N 2533/54* (2013.01); *C12N 2533/74* (2013.01); *C12N 2537/10* (2013.01)

(58) Field of Classification Search
CPC ................ C08J 2405/10; C08J 2405/04; C08J 2305/04; C08J 3/075; A23L 17/00; A23L 13/00
See application file for complete search history.

(56) References Cited

FOREIGN PATENT DOCUMENTS

| | | |
|---|---|---|
| CN | 109464700 A | 3/2019 |
| CN | 110302427 A | 10/2019 |
| CN | 110713727 A | 1/2020 |
| CN | 111303452 A | 6/2020 |
| CN | 112778644 A | 5/2021 |
| KR | 20170078417 A | 7/2017 |
| KR | 20180011656 A | 2/2018 |
| WO | 2010124655 A1 | 11/2010 |

\* cited by examiner

METHOD OF PREPARING CROSSLINKED HYDROGELS, RESULTING MUSCLE STEM CELL CULTURE MEDIA, AND METHODS OF USE

TECHNICAL FIELD

The present disclosure a crosslinked hydrogel for muscle stem cell culture and a preparation method and use thereof, particularly to a preparation method and use of a novel double-network enzymatically and physically crosslinked hydrogel, and belongs to the technical field of biological food materials.

BACKGROUND

Since over 90% of the world's population consumes meat, such mass consumption of meat causes a heavy burden to environment. Cultured meat from stem cells is obtained by a new technology for culturing meat in vitro using muscle cells. Currently, since the cultured meat has a potential for sustainable production, the development of the cultured meat is constantly accelerating. Compared with a traditional meat production, the production of the cultured meat from stem cells can relieve pains of animals and can also reduce the pollution of animal husbandry to the environment (Food & Agriculture Organization of the United Nations, 2006). Meanwhile, antibiotic abuse is common in the animal husbandry. Obviously, the cultured meat can solve the problem. However, the lack of an extensible cell culture substrate (scaffold) has become one of major challenges limiting the cultured meat from stem cells.

Nowadays, hydrogels extracted from natural biomaterials, such as polysaccharide-based materials (e.g., hyaluronic acid, chitosan, alginate, etc.) or protein-based materials (e.g., collagen, gelatin, etc.), have been widely used in stem cell scaffolds due to their good biocompatibility and biodegradability (Small, 2020, 16, 1-17). Alginate is widely available and inexpensive, has various excellent characteristics such as biocompatibility, and can interact with positive ions to form a dense three-dimensional "egg box" structure to improve mechanical properties. Polylysine (ε-PL) is a typical natural polyamino acid biomaterial containing about 25 repeating units of lysine, contains abundant positive charges, and has abundant biocompatibility, biodegradability and excellent water solubility. Collagen, a natural protein-based material, retains abundant bioactive sequences (e.g., RGD) and promotes cell adhesion and growth. However, natural hydrogels suffer from insufficient crosslinking and poor mechanical properties. Most crosslinking agents, such as glutaraldehyde and epoxy, have some toxicity, thus affecting the biocompatibility of the hydrogels. Therefore, it is still a challenge to prepare a natural hydrogel scaffold that is non-toxic and mechanically stable and has strong cell adhesion.

In addition, stemness maintenance and increased adhesion of muscle stem cells used for cultured meat become new challenges for hydrogel materials, and thus new requirements are provided for hydrogel properties. Muscle stem cells can be activated and proliferated by adding a growth factor bFGF. Nevertheless, the growth factor has a short residence time in a culture medium. Therefore, there is still no good solution to produce a natural hydrogel scaffold which is nontoxic, has good mechanical stability and strong muscle stem cell adhesion and can promote the muscle stem cells to maintain stemness.

SUMMARY

Technical Problems

In order to prepare a non-toxic natural hydrogel with high mechanical stability and strong cell adhesion and maintaining stemness of muscle stem cells, the present disclosure provides a novel double-network enzymatically and physically crosslinked hydrogel for culturing stem cells with strong adsorption force and not easy to collapse.

Technical Solutions

The present disclosure prepares a collagen/(ε-PL/heparan sulfate proteoglycan/alginate enzymatic and physical double-network hydrogel using TGase by combining an enzymatic method and a physical method. These modifying groups enable the hydrogel to adhere to cells and release growth factors in a controlled manner. Besides, after a large amount of water swelling, the double-network crosslinked structure enables the hydrogel to have enhanced mechanical property and maintain integrity through a synergistic effect of the two networks. At the same time, the hydrogel solve a problem of cytotoxicity caused by toxic chemical crosslinking agents used in a chemically crosslinked network.

The present disclosure provides a preparation method of a crosslinked hydrogel for muscle stem cell culture, where the method comprises the following steps: dissolving collagen to prepare a solution and adding alginate and heparan sulfate proteoglycan for being uniformly mixed with the collagen solution; and adding ε-PL and TGase into the solution, uniformly stirring, and putting a slurry into a mold for crosslinking to obtain the hydrogel.

Preferably, the method specifically includes the following steps:

(1) preparing the collagen solution: uniformly mixing and dissolving the collagen with an acetic acid aqueous solution to obtain the collagen solution;

(2) preparing a collagen/alginate solution: adding the alginate to the collagen solution prepared in step (1) and stirring until the alginate dissolves to obtain the collagen/alginate solution;

(3) preparing a collagen/alginate/heparan sulfate proteoglycan solution: adding the heparan sulfate proteoglycan to the collagen/alginate solution prepared in step (2) and stirring until the heparan sulfate proteoglycan dissolves to obtain the collagen/alginate/heparan sulfate proteoglycan solution;

(4) preparing a first physically crosslinked slurry: adding the polylysine ε-PL to the collagen/alginate/heparan sulfate proteoglycan solution prepared in step (3) and uniformly stirring to obtain the first physically crosslinked slurry;

(5) preparing a second enzymatically crosslinked slurry: adding the TGase to the first slurry prepared in step (4) and uniformly stirring to obtain the second enzymatically crosslinked slurry; and (6) preparing a hydrogel: putting the slurry obtained in step (5) into a mold, crosslinking for 12-36 h, and demolding to obtain the hydrogel for growth of muscle stem cells.

Preferably, the collagen includes one or a mixture of two or more of collagen, gelatin, hydrolyzed collagen, collagen polypeptide, and the like extracted from the skin of cattle, sheep, pigs, donkeys, poultry, aquatic animals, and the like, bovine achilles tendon, bone tissue, etc.

Preferably, in step (1), the acetic acid aqueous solution has a concentration of 0.02-0.05 mol/L.

Preferably, in step (1), the mass of the collagen is 10-15% of the mass of water.

Preferably, in step (2), the mass of the alginate is 15-25% of the mass of water.

Preferably, in step (2), the alginate has a viscosity of 4-12 cP.

Preferably, in step (3), the concentration of the heparan sulfate proteoglycan in the collagen/alginate/heparan sulfate proteoglycan solution is 200-500 μg/L.

Preferably, in step (4), the molar ratio of carboxyl group of the alginate to amino group of the ε-PL is 1:1 to 1:2

Preferably, in step (5), the amount of the TGase is 1-10% of the mass of the collagen.

Preferably, in step (6), the crosslinking is conducted at a temperature of 37-50° C.

The present disclosure provides a crosslinked hydrogel for muscle stem cell culture prepared by the preparation method.

The present disclosure provides a culture medium containing the crosslinked hydrogel for muscle stem cell culture.

The present disclosure provides a method for culturing muscle stem cells, where in the method, the crosslinked hydrogel for muscle stem cell culture is used as a culture medium.

Preferably, the muscle stem cells includes but be not limited to porcine muscle stem cells, bovine muscle stem cells, etc.

The present disclosure provides use of the preparation method or the crosslinked hydrogel for muscle stem cell culture in the field of cultured meat.

Beneficial Effects of the Present Disclosure

1. According to the slurry for preparing the hydrogel, with collagen and alginate as a base, the polylysine and the heparan sulfate proteoglycan are added, the collagen, the polylysine and the heparan sulfate proteoglycan form covalent crosslinking using the TGase, and a compact three-dimensional "egg box" network structure is formed through a physical electrostatic interaction between the polylysine and the alginate. The internally and externally dense hydrogel with a double crosslinked structure is formed by enzymatic and physical crosslinking.

2. The polylysine and the TGase are introduced into the hydrogel system to facilitate double enzymatic and physical crosslinking to obtain the hydrogel with higher mechanical strength.

3. The collagen is introduced into the hydrogel system and beneficial to adhering to stem cells and improving biocompatibility of the hydrogel.

4. The heparan sulfate proteoglycan is introduced into the hydrogel system and beneficial to immobilizing growth factors of stem cells, and can release the growth factors in a long term.

DETAILED DESCRIPTION

Embodiments of the present disclosure will be described in detail below with reference to embodiments, but those skilled in the art will understand that the following examples are only used to illustrate the present disclosure and should not be regarded as limiting the scope of the present disclosure. If no specific conditions are specified in the examples, the examples will be conducted according to conventional conditions or the conditions recommended by the manufacturer. All used reagents or instruments for which manufacturers are not specified are conventional commercially-available products.

TGase is purchased from Anhui Datang Bioengineering Co., Ltd., and has an activity of 109 U/g.

Alginate is purchased from Sigma-Aldrich and has a viscosity of 8 cP.

Figure 1:
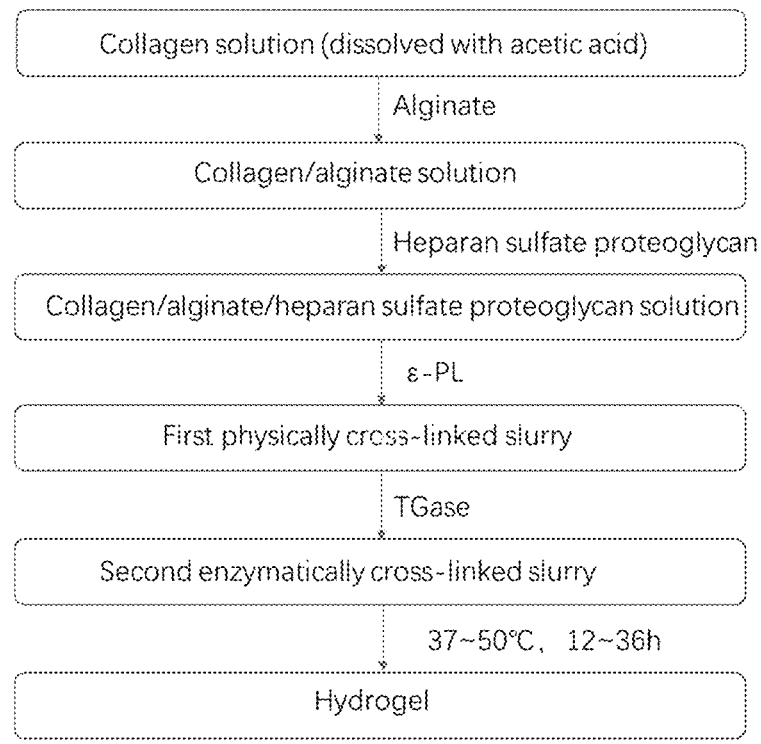
FIG. 1 is a flow chart of preparation of a collagen/ε-PL/heparan sulfate proteoglycan/alginate enzymatic and physical double-network hydrogel.
Figure 2:
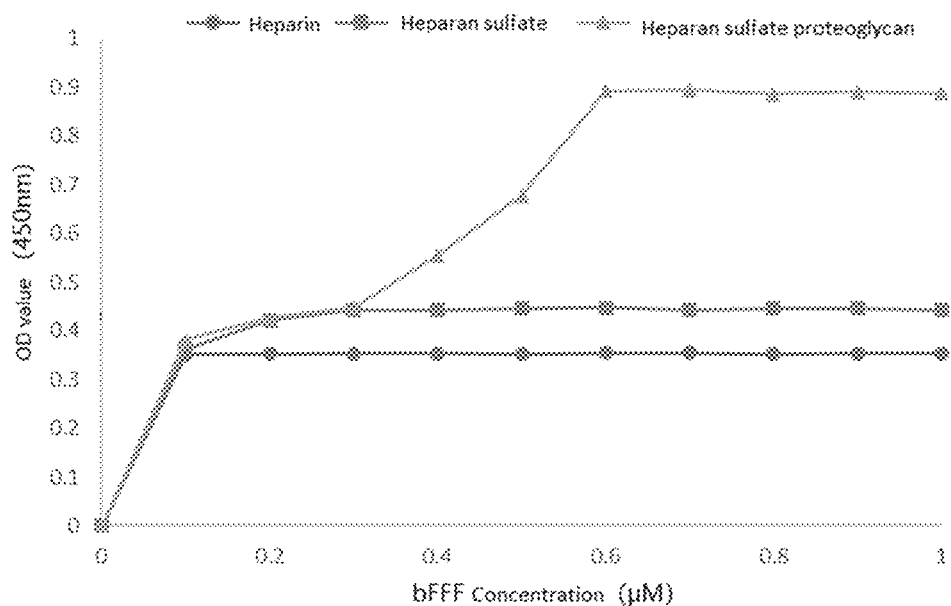
FIG. 2 is a graph showing an in-vitro binding efficiency of three heparins and derivatives thereof to bFGF.
Figure 3:
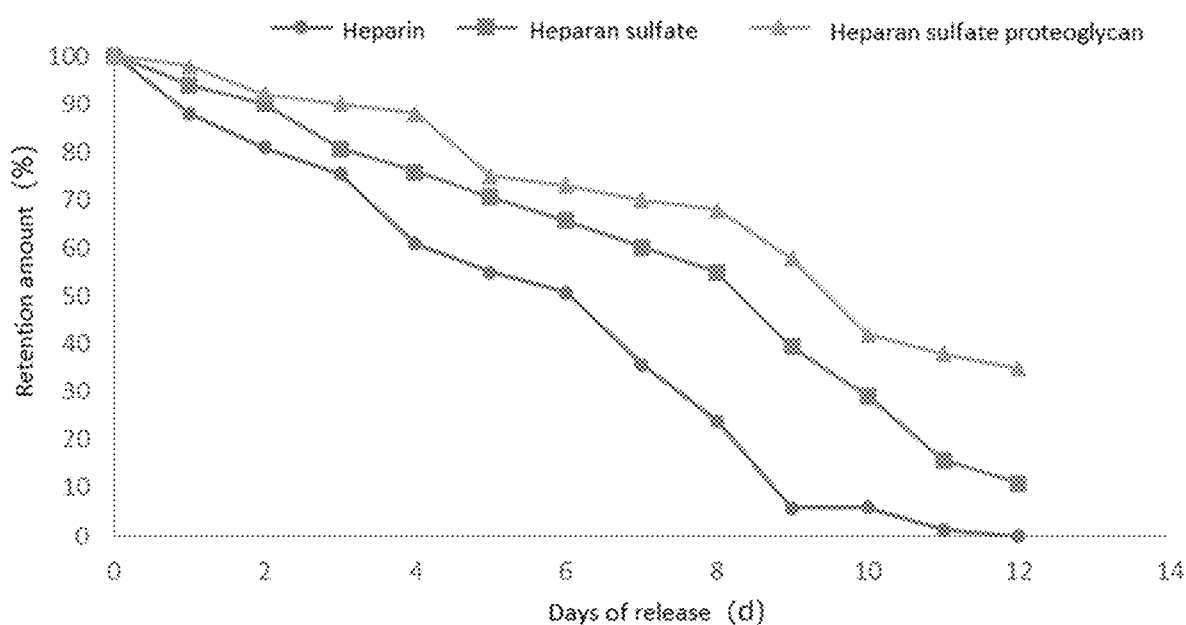
FIG. 3 is an in-vitro release profile of bFGF by three heparins and derivatives thereof.

Example 1 Preparation of Collagen/ε-PL/Heparan Sulfate Proteoglycan/Alginate Enzymatic and Physical Double-Network Hydrogel A hydrogel was prepared according to the flow chart in FIG. 1: 10 g of collagen was added to 100 mL of 0.02 mol/L acetic acid solution and stirred and dissolved to obtain a collagen solution. 15 g of alginate was added to the collagen solution and stirred and dissolved to obtain a collagen/alginate solution; 20 μg of heparan sulfate proteoglycan was added to the prepared solution to obtain a collagen/alginate/heparan sulfate proteoglycan solution; ε-PL with a molar ratio 1:1 of amino group of the ε-PL to carboxyl group of the alginate was added into the solution and stirred uniformly to obtain a first physically crosslinked slurry; and 0.1 g of TGase was added to the first slurry and stirred uniformly to obtain a second enzymatically crosslinked slurry. The slurry was put into a mold and crosslinked at 37° C. for 12 h and demolding was conducted to obtain a collagen/ε-PL/heparan sulfate proteoglycan/alginate enzymatic and physical double-network hydrogel. A large number of porcine muscle stem cells were observed after the porcine muscle stem cells were cultured on the hydrogel for 7 d. The hydrogel was freeze-dried in a vacuum freeze dryer (−80° C.) and had a porous structure with various pore sizes as observed by a scanning electron microscopy.

Example 2 Preparation of Collagen/ε-PL/Heparan Sulfate Proteoglycan/Alginate Enzymatic and Physical Double-Network Hydrogel A hydrogel was prepared according to the flow chart in FIG. 1: 15 g of collagen was added to 100 mL of 0.05 mol/L acetic acid solution and stirred and dissolved to obtain a collagen solution. 25 g of alginate was added to the collagen solution and stirred and dissolved to obtain a collagen/alginate solution; 50 μg of heparan sulfate proteoglycan was added to the prepared solution to obtain a collagen/alginate/heparan sulfate proteoglycan solution; ε-PL with a molar ratio 2:1 of amino group of the ε-PL to carboxyl group of the alginate was added into the solution and stirred uniformly to obtain a first physically crosslinked slurry; and 1.5 g of TGase was added to the first slurry and stirred uniformly to obtain a second enzymatically crosslinked slurry. The slurry was put into a mold and crosslinked at 37° C. for 36 h and demolding was conducted to obtain a collagen/ε-PL/heparan sulfate proteoglycan/alginate enzymatic and physical double-network hydrogel. A large number of porcine muscle stem cells were observed after the porcine muscle stem cells were cultured on the hydrogel for 7 d. The hydrogel was freeze-dried in a vacuum freeze dryer (−80° C.) and had a porous structure with various pore sizes as observed by a scanning electron microscopy (SEM).

Example 3 Adsorption of Growth Factors by Hydrogel

Growth factor adsorption experiment: the double-network enzymatically-physically crosslinked hydrogel (in Examples 1 and 2) was washed with PBS, the obtained hydrogel was dipped in 75% ethanol for 20 min and repeatedly dipped in sterile deionized water for 5 min, the ethanol was washed with sterile water three times to remove all residual ethanol (Food Hydrocolloids, 2017, 72, 210-218), the hydrogel was transferred to a solution containing growth factors of vitamin C (0.05 μg/mL) and bFGF (10 ng/mL), and the hydrogel adsorbing the growth factors was obtained after swelling for 24 h. The content of the bFGF (450 nm) and the vitamin C (536 nm) in the remaining solution was detected by an enzyme-linked immunosorbent assay (ELISA), and adsorption to the growth factors by the hydrogel was calculated according to differences between initial concentrations of the bFGF and the vitamin C in the solution and the concentrations in the remaining solution.

The results show that the hydrogel of Examples 1 and 2 can absorb all growth factors, indicating that the hydrogel prepared by the method of the present disclosure is helpful for adsorbing the growth factors.

Example 4 Release of Growth Factors by Hydrogel

Growth factor release experiment: the hydrogel adsorbing the growth factors in Example 3 was put into 1 mL of sterile PBS solution, the PBS solution in the experiment was collected using a pipette every 24 h, an equal volume of new sterile PBS solution was added, and the solution collected from a well plate was stored in an EP tube and placed in a −20° C. refrigerator for detection. The concentration of the bFGF (450 nm) and the content of the vitamin C (536 nm) in the collected solution were detected by an enzyme-linked immunosorbent assay (ELISA).

According to the growth factor release experiment, the bFGF and the vitamin C adsorbed by the hydrogel in Example 1 was still detectable on the 12th day, the bFGF and the vitamin C adsorbed by the hydrogel in Example 2 was still detectable on the 12th day, and thus the results of Examples 1 and 2 showed no significant difference. It can be seen that the prepared hydrogel is beneficial to immobilizing growth factors of stem cells and can release the growth factors in a long term.

Example 5 Culture of Porcine Muscle Stem Cells on Double-Network Hydrogel

Figure 4A:
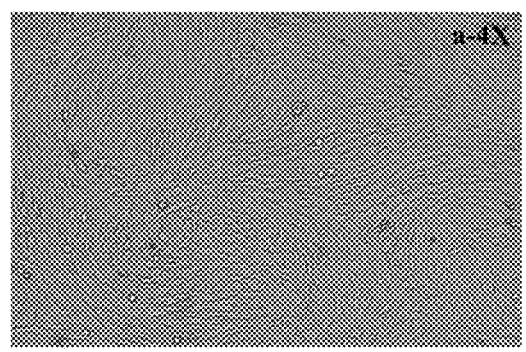
FIG. 4A is a microscopic image (4×) of primary porcine muscle stem cells cultured by the hydrogel prepared in Example 1 before differentiation.
Figure 4B:
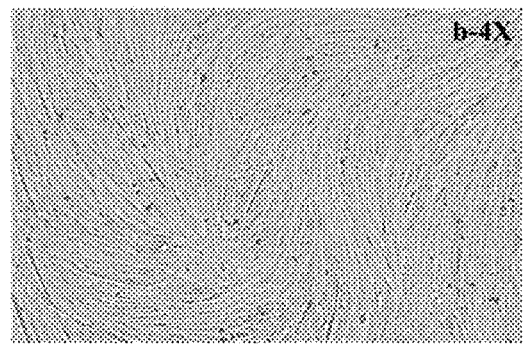
FIG. 4B is a microscopic image (4×) of primary porcine muscle stem cells cultured by the hydrogel prepared in Example 1 72 h after differentiation.

The hydrogel in Example 1 was subjected to the experiment of Example 3 to obtain the hydrogel containing the growth factors and cells were seeded on the prepared enzymatic and physical double-network hydrogel at a density of 1.500 cells/mm$^2$ and incubated in a growth medium (79% DMEM, 10% FBS, 1% double antibodies, 79% DMEM) for 24 h. The cells are cultured in a differential medium (97% of DMEM, 2% of horse serum and 1% of double antibodies) for 7 d. A large number of significantly proliferating cells were observed after 7 d of culture. The results are shown in FIG. 4A and FIG. 4B.

Example 6 Mechanical Testing of Hydrogel

The hydrogel was tested in uniaxial compression using an Instron mechanical test frame (model 5565A). Stress was calculated from a force curve $$\sigma = \frac{F}{A_0},$$

where F is a force used to compress a sample and $A_0$ is an initial area of the sample. Modulus of gel was calculated by $$G(t) = \frac{\sigma(t)}{\gamma}.$$

The sample was tested in triplets. Before testing, the hydrogel was carefully examined for cracks or deformation. The hydrogel was aligned in the center of a stainless steel compression plate. The hydrogel was slippery and can expand freely when compressed. The stress relaxation of the sample was investigated under compression of 5%, 10% and 20% strain using an initial crosshead speed of 4% strain/sec.

The study found that when the hydrogel prepared in Example 1 by the present disclosure was relaxed, it had a stress response as long as 290 s; and when the hydrogel prepared in Example 2 by the present disclosure was relaxed, it had a stress response as long as 300 s.

Example 7 Preparation of SEM Hydrogel Sample

Figure 5A:
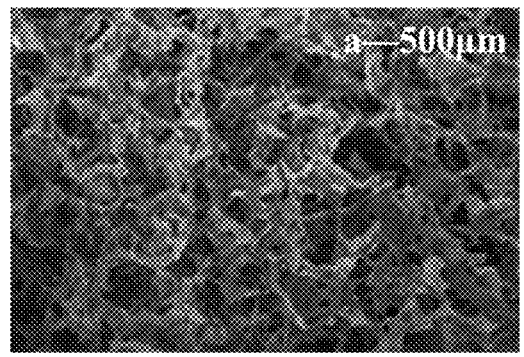
FIG. 5A is a scanning electron microscopy (SEM) image of the hydrogel prepared in Example 1 under 500 μm.
Figure 5B:
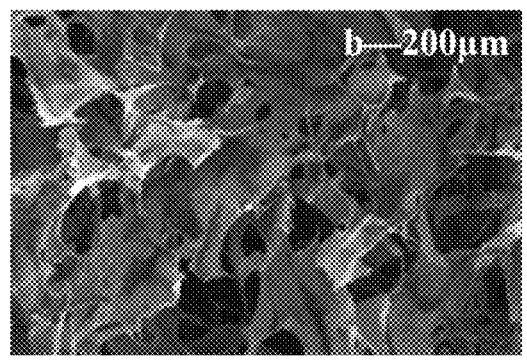
FIG. 5B is a scanning electron microscopy (SEM) image of the hydrogel prepared in Example 1 under 200 μm.
Figure 6:
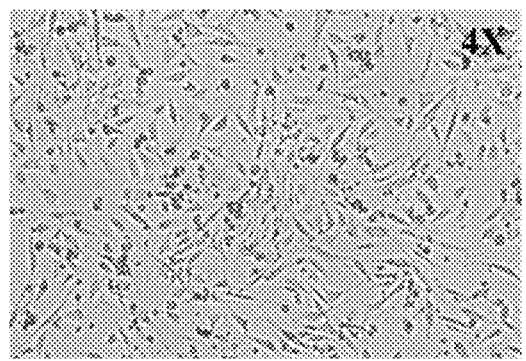
FIG. 6 is a microscopic image of primary muscle stem cells cultured by the hydrogel prepared in Comparative example 1.
Figure 7:
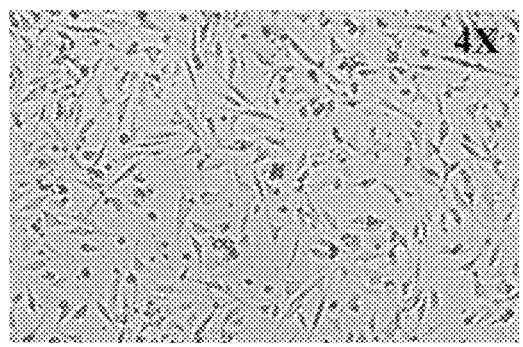
FIG. 7 is a microscopic image of primary muscle stem cells cultured by the hydrogel prepared in Comparative example 2.
Figure 8:
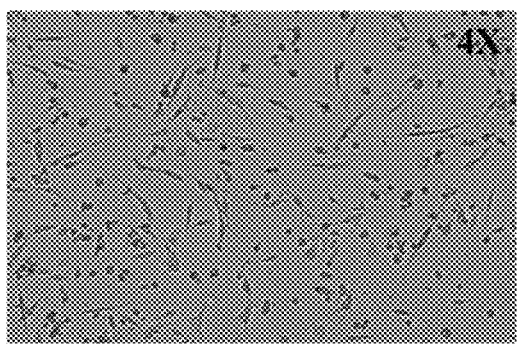
FIG. 8 is a microscopic image of primary muscle stem cells cultured by the hydrogel prepared in Comparative example 3.
Figure 9:
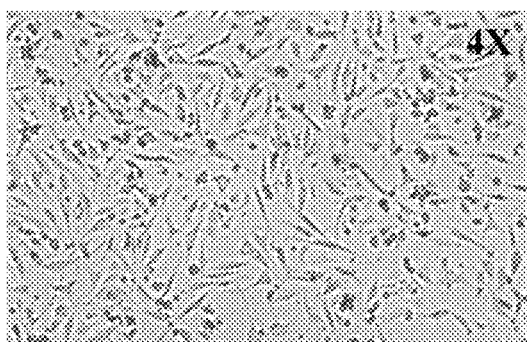
FIG. 9 is a microscopic image of primary muscle stem cells cultured by the hydrogel prepared in Comparative example 4.
Figure 10:
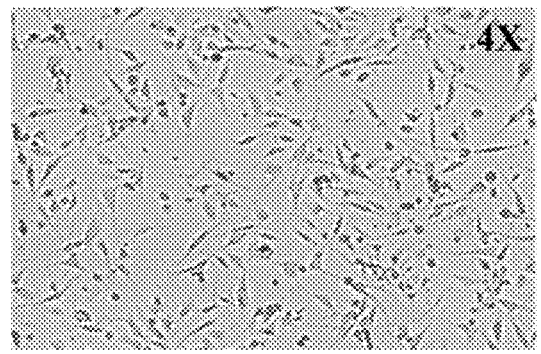
FIG. 10 is a microscopic image of primary muscle stem cells cultured by the hydrogel prepared in Comparative example 5.

Morphology of the freeze-dried hydrogel was imaged using a Hitachi S-4800 SEM (Hitachi, Japan) with an accelerating voltage of 5 kV. Before testing, a cross-section of the hydrogel was fixed on a metal substrate with a conductive tape and sputter-coated with gold. The study found that the hydrogel prepared by the present disclosure had a porous structure with various pore sizes (shown in FIG. 5A and FIG. 5B) and the structure was beneficial to the swelling of growth factors and promoted diffusion of the growth factors into the hydrogel. Moreover, the pores had a relatively large specific surface area and were conducive to the adhesion of muscle stem cells.

Comparative Example 1

Only alginate was not added, other steps were the same as in Example 1, and an enzymatically crosslinked hydrogel was obtained.

The growth factor adsorption experiment was conducted according to Example 3. It was found that when growth factors were adsorbed for 24 h, the hydrogel had collapse with a proportion of 8%. The prepared hydrogel was subjected to stress testing and only had a stress response of 150 s. A small amount of porcine muscle stem cells were observed after the porcine muscle stem cells were cultured on the hydrogel for 7 d.

The results showed that in the absence of the alginate, the prepared hydrogel had significantly worse adsorption to the growth factors and significantly worse swelling and mechanical properties, and was not beneficial to culturing the muscle stem cells.

Comparative Example 2

Only collagen and TGase were not added, other steps were the same as in Example 1, and a hydrogel was obtained.

The growth factor adsorption experiment of Example 3 was conducted on the prepared hydrogel. It was found that when growth factors were adsorbed for 24 h, the hydrogel had collapse with a proportion of 5%. The prepared hydrogel was subjected to stress testing and only had a stress response of 180 s. A small amount of porcine muscle stem cells were observed after the porcine muscle stem cells were cultured on the hydrogel for 7 d.

The results showed that in the absence of the collagen and the TGase, the prepared hydrogel had significantly worse adsorption to the growth factors and significantly worse swelling and mechanical properties, and was not beneficial to culturing the muscle stem cells.

Comparative Example 3

Only heparan sulfate proteoglycan was not added, other steps were the same as in Example 1, and a hydrogel was obtained.

The growth factor adsorption experiment was conducted on the prepared hydrogel. It was found that when growth factors were adsorbed for 24 h, the hydrogel adsorbed only a small amount of growth factors. The growth factor release experiment was conducted and no growth factor was detectable in the hydrogel after 2 d. The prepared hydrogel was subjected to stress testing and had a stress response of 285 s. A small amount of porcine muscle stem cells were observed after the porcine muscle stem cells were cultured on the hydrogel for 7 d.

Comparative Example 4

15 g of alginate was added to 50 mL of deionized water and stirred to obtain an alginate solution, ε-PL with a molar ratio 1:1 of amino group of the ε-PL to carboxyl group of the alginate was added into the solution and stirred uniformly to obtain a first physically crosslinked slurry; 10 g of collagen was dissolved with 50 mL of 0.04 mol/L of acetic acid solution to obtain a collagen solution, and 20 μg of heparan sulfate proteoglycan was added to the collagen solution and stirred uniformly to obtain a solution; and the solution was poured into the first slurry for being mixed and stirred uniformly, and 0.1 g of TGase was added to the slurry and stirred uniformly to obtain a second enzymatically crosslinked slurry. The slurry was put into a mold and crosslinked at 37° C. for 12 h and demolding was conducted to obtain a hydrogel. A small amount of porcine muscle stem cells were observed after the porcine muscle stem cells were cultured on the hydrogel for 7 d.

Comparative Example 5

10 g of collagen was added to 50 mL of 0.04 mol/L acetic acid solution and stirred and dissolved to obtain a collagen solution. 0.1 g of TGase was added to the collagen solution and stirred uniformly to obtain a gel; and 15 g of alginate was added to 50 mL of deionized water and stirred to obtain an alginate solution, 20 μg of heparan sulfate proteoglycan was added to the solution and stirred uniformly, ε-PL with a molar ratio 1:1 of amino group of the ε-PL to carboxyl group of the alginate was added and stirred uniformly to obtain a physically crosslinked slurry, the slurry was mixed with the gel, an obtained gel material was placed into a mold and crosslinked at 37° C. for 12 h, and demolding was conducted to obtain a hydrogel. A small amount of porcine muscle stem cells were observed after the porcine muscle stem cells were cultured on the hydrogel for 7 d.

Although the present disclosure has been disclosed as above in the preferred examples, it is not intended to limit the present disclosure. Any person skilled in the art can make various changes and modifications without departing from the spirit and scope of the present disclosure. Therefore, the protection scope of the present disclosure should be as defined in the claims.

What is claimed is:
1. A method of preparing a crosslinked hydrogel, which comprises:
    uniformly mixing and dissolving collagen with an acetic acid aqueous solution to obtain a collagen solution;
    adding alginate to the collagen solution and stirring until the alginate dissolves to obtain a collagen/alginate solution;
    adding heparan sulfate proteoglycan to the collagen/alginate solution and stirring until the heparan sulfate proteoglycan dissolves to obtain the collagen/alginate/heparan sulfate proteoglycan solution;
    adding ε-polylysine (ε-PL) to the collagen/alginate/heparan sulfate proteoglycan solution and uniformly stirring to obtain a first physically crosslinked slurry;
    adding transglutaminase (TGase) to the first physically crosslinked slurry and uniformly stirring to obtain an enzymatically crosslinked slurry; and
    pouring the enzymatically crosslinked slurry into a mold, incubating the enzymatically crosslinked slurry in the mold for 12-36 hour, and
    demolding the enzymatically crosslinked slurry to obtain the hydrogel.
2. The method of claim 1, wherein acetic acid aqueous solution is added at a concentration of 0.02 mol/L to 0.05 mol/L, and wherein the collagen is 10% to 15% by mass of water in the acetic acid aqueous solution.
3. The method of claim 1, wherein the alginate is 15% to 25% by mass of water in the acetic acid aqueous solution.

4. The method of claim 1, wherein the heparan sulfate proteoglycan in the collagen/alginate/heparan sulfate proteoglycan solution is 200 µg/L to 500 µg/L.

5. The method of claim 3, wherein the heparan sulfate proteoglycan in the collagen/alginate/heparan sulfate proteoglycan solution is 200 µg/L to 500 µg/L.

6. The method of claim 1, wherein the molar ratio of carboxyl groups of the alginate to amino groups of the ε-PL is 1:1 to 1:2; and wherein TGase is present at 1% to 10% by mass of the collagen.

7. The method of claim 3, wherein the molar ratio of carboxyl groups of the alginate to amino groups of the ε-PL is 1:1 to 1:2; and wherein TGase is present at 1% to 10% by mass of the collagen.

8. A crosslinked hydrogel for muscle stem cell culture prepared by the preparation method of a crosslinked hydrogel for muscle stem cell culture according to claim 1.

9. A method for culturing muscle stem cells, wherein in the method, the crosslinked hydrogel for muscle stem cell culture according to claim 8 is used as a culture medium.

* * * * *